United States Patent [19]
Olson et al.

[11] Patent Number: 5,849,474
[45] Date of Patent: Dec. 15, 1998

[54] DIAGNOSIS OF PREECLAMPSIA IN MAMMALS

[76] Inventors: Camilla M. Olson, 805 Melville Ave., Palo Alto, Calif. 94301; Charles Peterson, 2219 Bath St., Santa Barbara, Calif. 93105

[21] Appl. No.: 567,941

[22] Filed: Dec. 6, 1995

[51] Int. Cl.$^6$ .............................. A61K 49/04; G01N 1/00
[52] U.S. Cl. .................... 435/4; 435/2; 435/7.4; 435/10; 435/15; 435/18; 435/25; 435/28; 435/973; 435/975
[58] Field of Search ................................. 435/2, 7.4, 973, 435/975, 10, 15, 18, 25, 28

[56] References Cited

U.S. PATENT DOCUMENTS

| | | |
|---|---|---|
| 5,079,171 | 1/1992 | Senyei et al. . |
| 5,108,898 | 4/1992 | Peters et al. . |
| 5,198,366 | 3/1993 | Silberman . |
| 5,238,819 | 8/1993 | Roberts et al. . |

OTHER PUBLICATIONS

Brown et al., "The Relationship of Maternal Erythrocyte Oxygen Transport Parameters to Intrauterine Growth Retardation," *Am. J. Obstet. Gynecol.,* vol. 162, pp. 223–229 (1990).

Conrad et al., "Identification of Increased Nitric Oxide by Biosynthesis During Pregnancy in Rats," *FASEB Juournal,* vol. 7, pp. 566–571 (1993).

Seligman et al., "The Role of Nitric Oxide in the Pathogenesis of Preeclampsia," *Am.J. Obstet. Gynecol.,* vol. 171, pp. 944–948 (1994).

Tsukimori et al., "The Superoxide Generation of Neutrophils in Normal and Preeclamptic Pregnancies," *Obstet. Gynecol.,* vol. 81, pp. 536–549 (1993).

Entman et al., "Increased Levels of Carboxyhemoglobin and Serum Iron as an Indicator of Increased Red Cell Turnover in Preeclampsia," *Am. J. Obstet. Gynecol.,* vol. 156, pp. 1169–1173 (1987).

Sagen et al., "Serum Urate as a Predictor of Fetal Outcome in Severe Preeclampsia," *Acta Obstetricia et Gynecologica Scandinavica,* vol. 63, pp. 71–75 (1984).

*Primary Examiner*—James O. Wilson
*Attorney, Agent, or Firm*—Patricia M. Drost; Nath & Associates

[57] ABSTRACT

An improved method of diagnosing preeclampsia comprising the steps of
  a. collecting blood from a pregnant female mammal; and
  b. detecting in said blood significantly elevated levels of at least one substance selected from the group consisting of:
    (1) a hemoglobin variant or hemoglobin variant precursor and
    (2) a red blood cell glycolytic enzyme or a red blood cell glycolytic enzyme precursor.

By detecting the presence of an appropriate "marker" in the blood, preeclampsia can be diagnosed at an earlier stage, thus making possible timely therapeutic intervention. An assay kit for detecting the markers is also provided.

13 Claims, 2 Drawing Sheets ium DIAGNOSIS OF PREECLAMPSIA IN MAMMALS

FIELD OF THE INVENTION

The present invention relates to the early detection of a marker for preeclampsia during pregnancy. In particular, the invention relates to testing the blood of a pregnant female mammal to detect significantly elevated levels of particular substances, thus enabling early diagnosis and clinical intervention when a preeclamptic condition is found.

BACKGROUND ART

Hypertension in pregnancy can lead to a range of disorders, from minor to life-threatening, as follows:

(1) Pregnancy-induced-hypertension: Hypertension alone.

(2) Preeclampsia: Diagnosed by development of hypertension plus proteinuria or edema that is generalized and overt, or both.

(3) Eclampsia: Diagnosed by convulsions precipitated by pregnancy-induced or -aggravated hypertension.

The most common hypertensive disorder in pregnancy is preeclampsia. Preeclampsia is classically described as a triad of symptoms, which includes not only hypertension but also edema and proteinuria. The severity of the syndrome is assessed by the frequency and intensity of the following indicators:

maternal elevated diastolic blood pressure, proteinuria, headache, visual disturbances, upper abdominal pain, oliguria, serum creatinine, thrombocytopenia, hyperbilirubinemia, liver enzyme elevation, pulmonary edema and/or distress, convulsions, and fetal grow retardation.

The more profound the frequency and intensity of these indicators, the more likely is the need for immediate delivery. However, the ability to differentiate between mild and severe preeclampsia cannot be pursued rigidly, because an apparently mild case of the disease may progress rapidly to the severe form, thereby risking the life of the mother.

While preeclampsia is primarily a disease of the mother, it can also significantly impact the health of the fetus. Many preeclamptic pregnancies result in low birth weight ("LBW") infants. The majority of neonates who fall into the LBW category do so because of prematurity. Some fall into this category because they have been growth-retarded in utero and are small for their gestational age. The most severely affected neonates are both premature and small for gestation age. The problems commonly associated with fetal growth are three-fold: decreased nutrient (amino acid and carbohydrate) transfer, decreased blood flow, and reduced oxygen transfer from the maternal to the fetal circulation.

Like other maternal disorders such as chronic hypertension, diabetes, and maternal collagen vascular diseases, preeclampsia is known to cause characteristic changes in the vasculature of the placenta. Specifically, preeclampsia is often associated with pathologic changes in the uteroplacental spiral arteries that supply the maternal intervillous space of the placenta. Upon postpartum examination, the spiral arteries are typically significantly narrowed or hardened and may even become completely infarcted.

These pathological changes cause reduced blood flow and limit the availability of oxygen and nutrients to the fetus. Subsequently, the fetus can become hypoxic and suffer from significant organ damage, intrauterine growth retardation ("IUGR"), and even death.

Oxygen, in both maternal and fetal blood, is transported in two ways: (1) physically dissolved in plasma and (2) reversibly bound to hemoglobin. Hemoglobin is a tetrameric protein in blood that fulfills many important roles physiologically, including the efficient delivery of oxygen via an allosteric mechanism. Hemoglobin takes up and releases oxygen at appropriate physiological pressures, is highly soluble, and has good buffering capabilities.

When bound to hemoglobin, up to four molecules of oxygen are attached to each molecule of hemoglobin. Oxygen binds to the four "hemes" of the hemoglobin molecule. Each "heme" contains porphyrin and iron in the ferrous state. The ferrous iron-oxygen bond is readily reversible. The binding of a first oxygen to a heme requires a great amount of energy, but less energy is required for binding the second oxygen. Even less energy is required for binding the third oxygen, and the least amount of energy is required to hold the fourth oxygen.

Hemoglobin has two I subunits and two J subunits arranged with twofold symmetry. The I and J dimers rotate during oxygen release to open a large central water cavity.

The binding at the $I_1$–$J_1$ interface is tighter than that of either the $I_1$—$I_1$ or the $I_1$–$J_2$ interfaces, and the allosteric transition involving movement of the I–J dimer takes place between the binding of the third and fourth oxygen.

The partial pressure of oxygen is a measure of the amount of oxygen physically dissolved in the water phase of plasma. It represents the oxygen pressure required to maintain that much oxygen dissolved in the blood. Since the majority of oxygen contained in blood is bound to hemoglobin, partial pressure measurements assess only about 2% of the oxygen contained in the blood.

Oxygen saturation refers to the percent of hemoglobin that is oxygenated. For example, a 95% saturation in an individual with 10 grams of hemoglobin means that 9.5 grams of the hemoglobin is oxygenated. Oxygen bound to hemoglobin typically represents about 97 to 98% of the total oxygen in the blood.

Frequently, an oxygen equilibrium curve is derived to determine the oxygen affinity and the degree of allosteric activity of an individual's hemoglobin. To do this, the partial pressure of oxygen in millimeters of mercury (mm Hg) is plotted along the X axis of a graph, and the resulting percentage of hemoglobin oxygenation is plotted on the Y-axis. When a horizontal line is drawn from the 50% oxygen saturation point on the Y axis to a point of intersection on the curve, and a vertical line is then drawn from this point of intersection to the X-axis, the X-intercept is known as the $P_{50}$ value. This $P_{50}$ value represents the partial pressure of oxygen in mm of Hg required to produce a level of 50% oxygen saturation in the hemoglobin sample being tested.

Under physiological conditions, i.e., at 370 C., pH=7.4, and using a partial carbon dioxide pressure of 40 mm Hg, the $P_{50}$ for normal adult hemoglobin ("HbA") is about 26.55 mm Hg. If a lower than normal $P_{50}$ value is obtained, the resulting curve is considered to be "left-shifted", indicating the presence of high-affinity hemoglobin. Conversely, if a higher than normal $P_{50}$ value is obtained, the curve is considered to be "right-shifted", and the presence of low-affinity hemoglobin is indicated.

In a normal pregnancy, the oxyhemoglobin dissociation curve shifts to the right due to a 30% increase in the production of 2,3-DPG, which increases the oxygen made available, not only to supply maternal tissues, but also for transport to the fetus. In contrast, the oxyhemoglobin dissociation curve in pregnant women with preeclampsia and growth retarded infants will be shifted to the left and accompanied by reduced concentrations of the natural allosteric modifier, 2,3-diphosphoglyceric acid ("2,3-DPG"). Brown et al., "The Relationship of Maternal Erythrocyte Oxygen Transport Parameters to Intrauterine Growth Retardation", *Am. J. Obstet. Gynecol.*, 162:223–29 (1990). The reason for this shift in 2,3-DPG levels is not clear.

Senyei et al., U.S. Pat. No. 5,079,171 issued 7 Jan. 1992, and Peters et al., U.S. Pat. No. 5,108,898 issued 28 Apr. 1992, each disclose that preeclampsia, pregnancy-induced hypertension, and eclampsia can be diagnosed by identifying the presence of an endothelial cell marker, cellular fibronectin, in a sample of blood, plasma or serum of a pregnant woman, for example, by using a sandwich or competition immunoassay. The cellular fibronectin derives from endothelial cells that are ruptured or disturbed during the disease process.

Silberman, U.S. Pat. No. 5,198,366 issued 30 Mar. 1993, discloses that antigenic compounds are released from the placental tissue into body fluids in a preeclamptic pregnancy. Silberman uses the radioassay of a particular protein specific to human placenta, known as "PP-13", to identify subjects having preeclampsia.

Roberts, U.S. Pat. No. 5,238,819 issued 24 Aug. 1993, discloses the diagnosis of preeclampsia using an assay to measure a mitogenic factor in blood. The mitogenic factor is a proteinaceous compound of about 160 kDa and is capable of stimulating fibroblast mitosis. Its presence is detected by detecting radio-labelled thymidine uptake by cells activated by the sera or plasma of a preeclamptic subject.

It is known that heme, the iron-containing compound that carries oxygen, is one of the handful of molecular cofactors tightly bound to the enzyme nitric acid synthase ("NOS") and helps the enzyme accomplish its task of producing NO. In blood vessels, NO is released by endothelial cells on the inside of the vessel wall, migrates to nearby muscle cells, and causes them to relax. The resulting dilation of the blood vessel causes lowering of the blood pressure. Some researchers have postulated that NO is involved in the normal vasodilatory responses of gestation and have speculated that, in preeclampsia, an insufficient production of NO underlies the hypertension and other manifestations of the disease. Conrad et al., "Identification of Increased Nitric Oxide by Biosynthesis During Pregnancy in Rats", *FASEB J.*, 7:566–71 (1993) and Seligman et al., "The Role of Nitric Oxide in the Pathogenesis of Preeclampsia", *Am. J. Obstet Gynecol.*, 171:944–48 (1994).

Another study has suggested that preeclampsia can be characterized by the presence of a neutrophil activator that enhances superoxide production, which is thought to contribute to the pathophysiologic changes observed in preeclampsia. Tsukimori et al., "The Superoxide Generation of Neutrophils in Normal and Preeclamptic Pregnancies", *Obstet. Gynecol.*, 81, 536–49 (1993).

It is also known that pregnant women with preeclampsia generally exhibit two, apparently contradictory, hematologic findings. They are, on the one hand, increased monoxyhemoglobin concentrations (Entman et al., "Increased Levels of Carboxyhemoglobin and Serum Iron as an Indicator of Increased Red Cell Turnover in Preeclampsia", *Am. J. Obstet. Gynecol.*, 156:1169–73 (1987)) and, on the other hand, increased hematocrit or hemoglobin concentration (Sagen et al., "Serum Urate as a Predictor of Fetal Outcome in Severe Preeclampsia", *Acta Obstetricia et Gynecologica Scandinavica*, 63:71–75 (1984)). The hematocrit changes are generally attributed to a reduction in plasma volume; carbon monoxide is usually produced as a result of heme catabolism; and the most likely source of carboxyhemoglobin has been thought to be increased hemolysis.

However, despite the well-described clinical course of preeclampsia and these theories, the exact etiology of the disorder remains unknown. The disease also remains untreatable, except by prompt delivery of the fetus and placenta. Left untreated or inadequately treated, women with preeclampsia are at risk for fetal hypoxia, fetal intrauterine growth retardation ("IUGR"), intrauterine fetal death, and even maternal death. Preeclampsia and other hypertensive disorders of pregnancy predispose the uteroplacental vessels to thrombosis. Extensive lesions of the placenta, with necrosis of more than 10% of the placental parenchyma, are most often found in women with preeclampsia.

Generally occurring in women during their first pregnancy, preeclampsia more commonly affects teenagers and women over 35 years of age. Women with underlying diseases that predispose them to hypertension are also among those at greater risk for the development of preeclampsia. The disorder affects about 7% of all pregnancies in the United States. The lack of therapy for preeclampsia, coupled with the age-old lack of ability to diagnose it until the pregnancy is near term, continues to stimulate a great deal of interest in searching for "markers" to enable detection of the condition at an earlier stage of the disease, thus offering more hope of meaningful treatment.

DISCLOSURE OF THE INVENTION

The inventors have now discovered that the reduced 2,3-DPG levels in preeclamptic women may indicate the interruption of glycolysis and that the resulting decrease in ATP production may, in turn, result in increased hemolysis. If the abnormal changes seen in preeclampsia are accompanied by a change in glycolysis, then it is theorized that the resulting interruption of a specific metabolic step could change the relative proportions of even "minor" hemoglobins in maternal blood. For instance, the accumulation of varying amounts of glycolytic intermediates could be forming adducts with hemoglobin in a manner similar to that formed in producing the elevated glycated hemoglobin levels commonly associated with diabetes mellitus. Specifically, two types of such markers, and thus a method for diagnosing preeclampsia, have now been discovered.

The method of the invention comprises the steps of:

a. collecting blood from a pregnant female mammal; and b. detecting in the blood significantly elevated levels of at least one substance selected from the group consisting of:

(1) a hemoglobin variant or hemoglobin variant precursor and (2) a red blood cell glycolytic enzyme or a red blood cell glycolytic enzyme precursor.

In another embodiment, an assay kit for diagnosing preeclampsia comprises a means for detecting in the blood of a pregnant female mammal significantly elevated levels of at least one hemoglobin variant (or hemoglobin variant precursor) and a red blood cell glycolytic enzyme (or red blood cell glycolytic enzyme precursor).

BRIEF DESCRIPTION OF DRAWING

The present invention will be more clearly understood by referring to the following drawing, in which.

MODES OF CARRYING OUT THE INVENTION

Figure 1A:
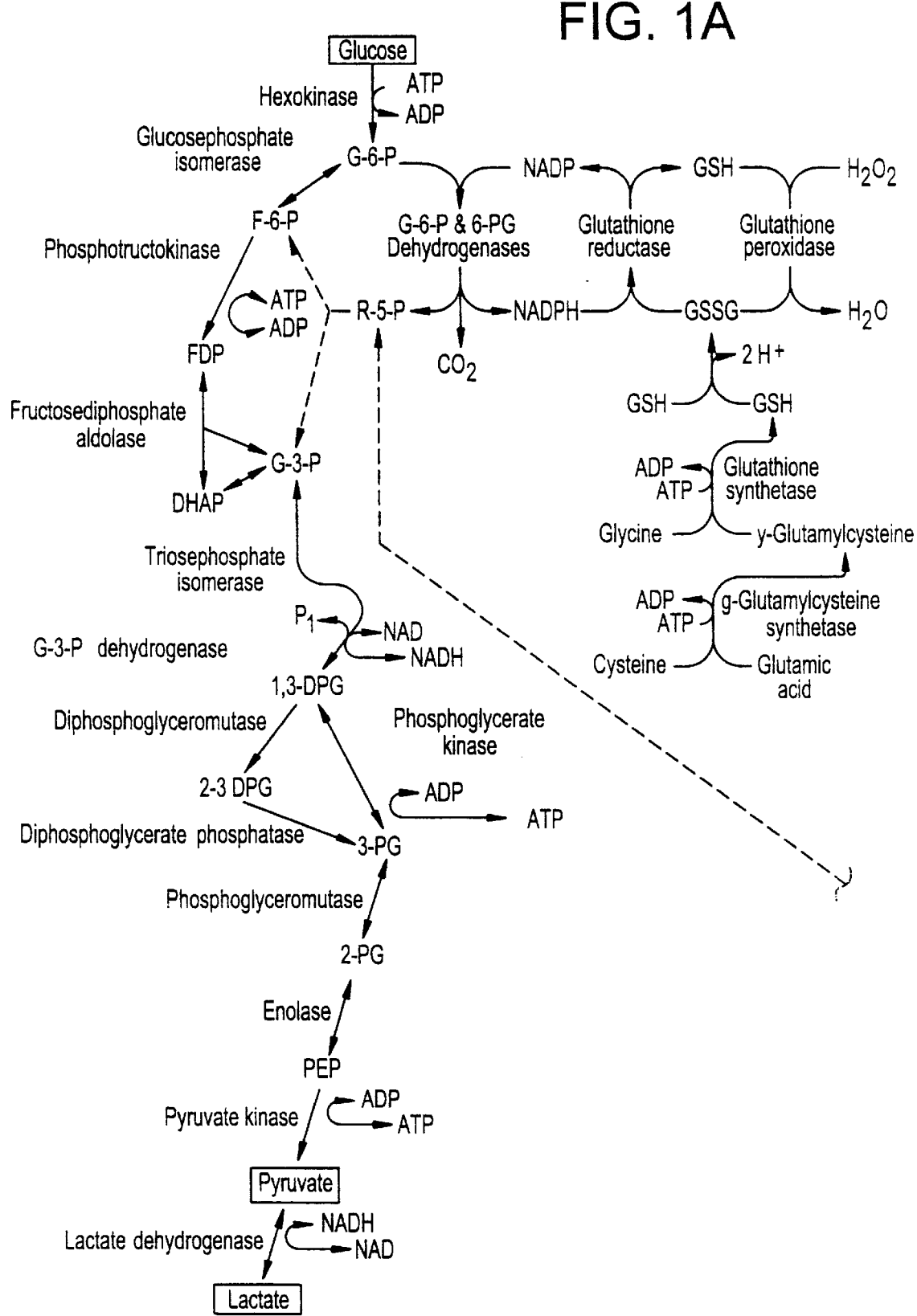
FIG. 1 illustrates the biochemical pathways of metabolism in an erythrocyte.

As used in this application, the term "preeclampsia" is defined in accordance with criteria established by the committee on Terminology of the American College of Obstetrics and Gynecology, that is, hypertension plus proteinuria, overt edema, or both.

The method of the invention is applicable to any animal that is a "placental" animal, i.e., one that nurtures the unborn fetus through a placenta. Such animals include, among others, humans, other primates, mammalian food animals, and pets.

The substance detected in the method and the assay of the invention can be either a hemoglobin variant (or hemoglobin variant precursor) or any one of a variety of red blood cell glycolytic enzymes (or red blood cell glycolytic enzyme precursors). The hemoglobin variant of the invention can be any variant that can significantly discriminate between pregnant subjects with and without preeclampsia.

Normal hemoglobin (hemoglobin $A_O$) performs the usual functions relating to oxygen transport, solubility and buffering capability, very well. In contrast, a minor portion of hemoglobin, usually in the form of a hemoglobin variant, may be by itself inadequate with respect to one or more of these functions. Some of the hemoglobin variants, sometimes called "minor hemoglobins", are composed of different polypeptide (globin) chains attached to the heme group, while others are composed of the same chains as normal hemoglobin $A_O$, but with post-translational modifications.

The variants having different polypeptide chain sequences are the products of genes other than the gene encoding the $A_O$ chains. Genetic factors or the accumulation of toxins can cause the overexpression of these variants.

The variant hemoglobins that result from the post-translational modification of the globin chains generally have a small molecule bound to the amine terminus of one or more chains. Hyperglycemic patients, such as those with diabetes mellitus or gestational diabetes, often have elevated hemoglobin $A_1$ levels. While the test for hemoglobin $A_1$ itself is usually not a significant marker for preeclampsia, the combination of $A_1$, $A_O$, and other minor hemoglobins that exhibit similar chromatographic behavior, often can be used to distinguish pregnant placental animals having preeclampsia from those having normal pregnancies.

In addition, glycated hemoglobin levels can be significantly elevated in preeclamptic subjects and, thus, may also serve as a useful indicator. Glycated hemoglobin is typically a better discriminator than $A_1$, possibly due to the superior precision that can be achieved with assays for glycated hemoglobin, i.e., coefficient of variation of 1–2% for glycated hemoglobin versus 10% or more for $A_1$. As test methods change and improve, therefore, other hemoglobin variants may also emerge as good markers for preeclampsia.

Other potentially useful hemoglobin variants include adducts of phosphorylated glycolytic intermediates and hemoglobin that generally chromatographs prior to hemoglobin $A_{1c}$ on cation exchange chromatography. Examples of useful hemoglobin variant precursors include those variants that chromatograph before $A_O$ upon cation exchange chromatography.

Figure 1B:
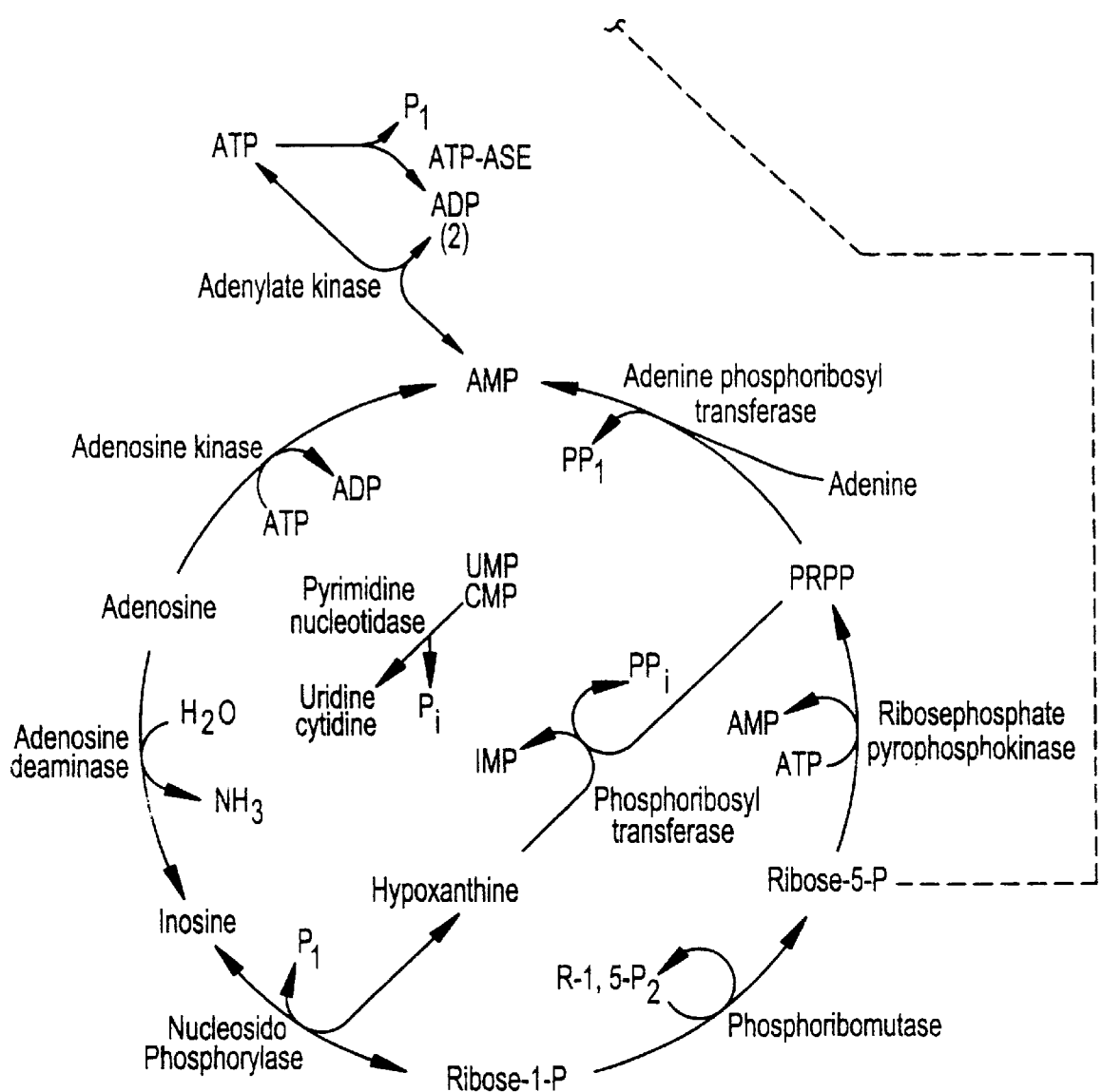

Another category of useful, detectable substances are red blood cell glycolytic enzymes (and precursors thereof), particularly those that are indicators for increased hemolysis, which tend to reflect stresses that are being placed on the glycolytic pathway. In the biochemical pathways of metabolism that take place in the erythrocyte, as shown in FIG. 1, glucose-6-phosphate is isomerized to fructose-6-phosphate. Fructose-6-phosphate is the substrate for a major rate-limiting reaction, phosphorylation at the carbon-1 position (mediated by the enzyme phosphofructokinase). The product of this reaction, fructose-1,6-phosphate, is produced at a cost of two moles of ATP. However, it is subsequently cleaved into dihydroxyacetone phosphate and D-glyceraldehyde-3-phosphate in an aldolase reaction to provide these two triose moieties. Each of these trioses may serve as a substrate for rephosphorylation of ADP by phosphoglycerate kinase and pyruvate kinase, thus generating four moles of ATP.

The elevation of pyruvate kinase (low substrate) levels is particularly useful in identifying potential preeclamptic patients, which may indicate a compensatory response for hemolysis. The usual indicators of increased hemolysis are decreased levels of glyceraldehyde phosphate dehydrogenase and glucose-6-phosphate dehydrogenase ("G6PD"). If hemolysis is a major factor in the preeclamptic subject, a decreased level of pyruvate kinase would be expected. While the pyruvate kinase levels are, in fact, slightly lower for preeclamptic subjects, in contrast, the low substrate pyruvate kinase levels unexpectedly tend to be higher.

Other potentially useful enzyme indicators include glyceraldehyde phosphate dehydrogenase, G6PD, phosphoglycerate kinase.

Straightforward procedures can be used to determine whether a compound exhibits the physiological activity necessary to function as a useful marker. For instance, as noted above, uric acid measurements may provide useful discrimination.

Thus, certain hemoglobin variants, glycolytic enzymes, and their precursors, optionally, in addition to other determinants such as red cell volume or hematocrit or uric acid, can function as good discriminating factors in distinguishing preeclamptic subjects from control subjects having normal pregnancies. The combination of these factors may provide an even better means of predicting the occurrence of preeclampsia than either factor alone and, thus, significantly improve the opportunity to provide timely therapeutic intervention.

In the method and assay of the invention, a blood sample is collected from the subject to be tested by conventional procedures. The sample can be collected from a capillary, an artery or a vein. If only enzymes are being tested for and not hemoglobin variants, the blood sample can be treated with EDTA and centrifuged to remove cells, yielding plasma. Alternatively, the blood sample may be clotted and the serum separated from the clot. The blood sample could also be absorbed by an absorbent material, such as paper, a fibrous material, or some other insoluble support to which the detectable substance could bind, and then would be dried for subsequent testing at a convenient time. Of course, an important condition for this last method is that the collection and drying procedure not degrade or otherwise deleteriously affect the enzyme or hemoglobin variant being tested for. The blood sample could be fresh or frozen. Additional specimens may be collected and then kept frozen, for example, at a temperature of about −800 C., for subsequent completion of additional tests on the thawed sample or for re-analysis to confirm the reproducibility of results obtained. In a preferred embodiment, however, the blood sample is freshly collected from the animal's general circulation, most preferably by venipuncture.

The detection of the enzyme or hemoglobin variant marker can be accomplished by any suitable procedure. For example, glycated hemoglobin can be determined by boronate affinity, high performance liquid chromatography, electrophoresis or chemical analysis following hydrolysis and the like. Other hemoglobin variants, or combination of variants, can be detected by examining the spectra of sequentially eluting fractions by cation exchange chromatography or electrophoretic analysis and the like.

The enzyme pyruvate kinase can be detected and quantified by measuring the ability of a hemolysate to form pyruvate from ADP and phosphoenolpyruvate, preferably at low concentrations. The enzyme G6PD can be assayed by measuring the rate that NADP is reduced in the presence of the sample. Other red blood cell glycolytic enzymes which can be measured are hexokinase, glucose phosphate isomerase, phosphofructokinase, aldolase, triose phosphate isomerase, diphosphoglycerate mutase, enolase, glucose-6-phosphate dehydrogenase, pyruvate kinase, lactate dehydrogenase, glutathione reductase and glutathione peroxidase. Methods to quantitate these enzymes are known to those skilled in the art.

Examples of useful red blood cell glycolytic enzyme products with hemoglobin include those that comprise fast-eluting species prior to $HbA_O$ upon cation exchange chromatography.

The sample size of the blood collected is varied according to individual needs and sensitivities. The amount of blood collected can vary widely, depending on the type of testing being used, the number of substances being tested for, the site of collection, and the possibility of any adverse effects to the mother or fetus. Typically, the blood sample size is somewhere in the range from about 25 to about 60 ml, preferably from about 45 to about 50 ml.

More than one indicator can be monitored at the same time in the method of the invention. In this event, however, the sample size will need to be large enough to complete all of the assays desired.

The method of the invention may also be useful to detect a number of other related diseases in pregnancy such as sepsis and hemorrhagic shock. It is also believed to be useful for any process having a central pathophysiology involving either general or local tissue hypoperfusion and dysoxia, since the hallmark of preeclampsia is intermittent hypoperfusion of various maternal tissue beds and organs.

An assay kit to be used in the method of the invention comprises any of the above-described detection means, either singly or in combination. Particularly preferred assay kits contain analyte standard, reagents for assays, a nomogram against which to compare results and a calculator/computer to calculate risk. The invention will be further clarified by the following examples, which are intended to be purely illustrative of the invention.

EXAMPLE 1

Pilot Study on Pregnant Women with Preeclampsia

This experiment was a case-control study in which eight pregnant women with preeclampsia were paired with eight suitable, asymptomatic pregnant women. Pairing was based on maternal age (±one year), number of weeks gestation (±one week), and ethnicity.

Subjects from an academic obstetrics practice were offered participation in the study unless they had a history of ingesting drugs other than iron supplements, had chronic hypertension, or were smokers. An increase in blood pressure of at least 30 mm Hg systolic, or 15 mm Hg diastolic, over the individual's pre-pregnancy readings was termed "hypertension" if confirmed over at least a six-hour interval. Proteinuria was defined as 0.3 gram or more protein in a 24-hour urine collection, or at least 0.1 g/liter in two random urine collections separated by at least six hours.

Blood samples of 53.5 ml for analysis were obtained upon the initial diagnosis of preeclampsia and at comparable gestational ages for matched controls by venipuncture. Tests performed on all 16 subjects were erythrocyte count, leukocyte count, hemoglobin, hematocrit, MCV, MCH, MCHC, platelets, reticulocytes, differential, sodium, potassium, chloride, bicarbonate, serum phosphate (inorganic phosphorus), SGOT, SGPT, lactic dehydrogenase, total and direct bilirubin, serum haptoglobin, carboxyhemoglobin, glycated hemoglobin by affinity chromatography, changes in chromatographic species by cation exchange, quantification of aldehyde adducts by fluorigenic HPLC, erythrocyte enzymes glycolytic pathway enzymes, and CF1 (a red cell surface marker).

Specific tests used for the following variant hemoglobins were performed: glycated hemoglobin, whole blood associated acetaldehyde, and hemoglobin $A_{1c}-A_O$. These tests are described below.

(1) Glycated Hemoglobin: Glycated hemoglobin, glycated serum protein, and glycated plasma protein concentrations were determined by boronate affinity, high performance liquid chromatography ("HPLC"; apparatus commercially available from Primus Corporation, Kansas City, Mo.). Inter- and intra-assay precision for this method is such that there is less than a 3% variation for both high and low values. The nondiabetic mean value for nonpregnant individuals is 5.50±0.50 using this assay (one standard deviation).

(2) Whole Blood Associated Acetaldehyde ("WBAA"): To determine whether ethanol exposure or abnormal endogenous metabolism might differ between the test group and the control group, a WBAA test was used. This assay has been shown to separate subjects based on ethanol exposure in mice, pigs, and humans. In this assay procedure, 250 TL of cyclohexanedione reagent was allowed to react with 250 TL of hemolysate for one hour at 700 C. to determine the amount of acetaldehyde associated with hemoglobin. The concentration of hemoglobin was determined by measuring the absorbance at 540 nm using the method of Drabkins, *Am. J Med. Sci.*, 217:710–11 (1949). Then the concentration of acetaldehyde was determined by high performance liquid chromatography ("HPLC"). HPLC samples were prepared by spinning the reaction mixture 2×15 minutes (40 C.; 16,000×g). The aqueous supernatant liquid was injected directly into the liquid chromatography apparatus, and the results were read as TM acetaldehyde in whole blood. The amount of acetaldehyde was determined directly as whole blood-associated acetaldehyde or by comparing the results with the standard curve of acetaldehyde concentrations. The proportion in nanomoles of acetaldehyde per gram protein was calculated by dividing the acetaldehyde concentration by the protein (hemoglobin) concentration. This measurement may also be calculated by dividing the acetaldehyde concentration by the plasma protein concentration.

(3) Separation of Hemoglobin Fractions by Cation Exchange Chromatography: A weak polyaspartic acid cation exchange column measuring 4.6 mm×200 mm (commercially available as "PolyCatA" from PolyLC Company in Columbia, Md.) and a guard column packed with the same materials were used for separating the hemoglobin fractions. The HPLC apparatus was equipped with a Rainin Dynamax HPLC Method Manager (version 1.4), a data acquisition system, and an HPLC controller.

Buffer A consisted of 35 mM bis[2-hydroxyethyl] iminotris[hydroxymethyl]-methane ("Bis Tris"), 3 mM ammonium acetate, and 1.53 mM potassium cyanide. The final pH was adjusted to 6.47 with 20% acetic acid. Buffer B consisted of 35 mM Bis Tris, 150 mM sodium acetate, 16.85 mM ammonium acetate, and 1.53 mM potassium cyanide. The final pH was adjusted to 6.8 with 20% acetic acid.

The column was equilibrated with a mixture of 35% buffer A and 15% buffer B at a flow rate of 1 mL/min for at least 20 minutes prior to each injection. The proportion of buffer B was increased from 15% at time 0 to 50% at 45 minutes' elapsed time and to 100% at 55 minutes' time elapsed. Buffer B remained at 100% for two minutes from 55 to 57 minutes, and then returned to 15% by 60 minutes.

A variable wavelength detector (commercially available from Beckman, Fullerton Calif.) was used to detect the eluting fractions at 415 nm.

The following two tests were used to assay the glycolytic enzymes pyruvate kinase and glucose-6-phosphate dehydrogenase ("G6PD").

(1) Pyruvate kinase: Measured using a standard assay of the ability of a hemolysate to form pyruvate from ADP and phosphoenolpyruvate. Normal values using this assay are about 2.0–8.8 U/g hemoglobin. The activity at low substrate concentration ("low substrate %") was determined with 0.25 mM phosphoenol pyruvate and 0.6 mM ADP.

(2) Glucose-6-phosphate dehydrogenase ("G6PD"): Determined by measuring the rate that NADP is reduced in the presence of G6PD.

In addition, gross red blood cell panels, blood chemistry panels, liver function profiles, and red blood cell enzymes were performed using standard clinical tests. Complete blood count was performed using an automated assay apparatus sold by Coulter. Statistical analyses were performed using the software programs "SYSTAT" (Evanston, Ill.) for discriminant analysis and "Statview" (from Abacus Concepts, Berkeley, Calif.) for unpaired t-tests.

Of the blood tests performed, those exhibiting statistically different values between the control group and the test group were uric acid, hematocrit, glyceraldehyde phosphate dehydrogenase, phosphoglycerate kinase, low substrate % pyruvate kinase, $G_6PD$, hemoglobin $A_{1c}$, glycated hemoglobin, and the hemoglobin $A_{1c}$–$A_O$ sum of chromatographic peak areas in the cation exchange chromatography of hemolysate. These values for some of these substances are summarized below in Table 1.

TABLE 1

Values for Selected Factors

| Test | Ave. for Control Group | Ave. for Preeclampsia Group | Range for Control Group | Range for Preeclampsia Group | Std. Dev. for Control Group | Std. Dev. for Preeclampsia Group |
|---|---|---|---|---|---|---|
| Pyruvate Kinase (Low Substrate) | 7.5 | 11.2 | 7.06 | 20.9 | 2.5 | 4.3 |
| Hematocrit | 34.1 | 37.2 | 8.7 | 15.7 | 2.8 | 3.1 |
| $A_{1c}$–$A_O$ Peak Area | 5.6 | 6.9 | 5.4 | 1.7 | 2.2 | 1.2 |
| Uric Acid | 3.7 | 5.7 | 0.6 | 0.4 | 0.7 | 0.6 |
| Glycated Hemoglobin | 5.04 | 5.4 | 0.2 | 0.11 | 0.4 | 0.3 |

Discriminant analysis of the tests named above indicated that the best discriminators between the control and the preeclamptic groups were: hematocrit, glycated hemoglobin, (low substrate %) pyruvate kinase and the $A_{1c}$–$A_O$ sum of chromatographic peak areas. The discriminant function obtained in the analysis was as follows:

$$0.407(\text{Hematocrit})+0.018(A_{1c}-A_O)+0.43(\text{glycated hemoglobin})+0.374(\text{low substrate pyruvate kinase})$$

Thus, as demonstrated by this study, at least one enzyme, low substrate pyruvate kinase and a number of hemoglobin variants were useful in detecting preeclampsia in pregnancy. It will be clear to those skilled in the art that modifications and/or variations of the disclosed subject matter can be made without departing from the scope of the invention claimed below.

We claim:

1. A method for the diagnosis of preeclampsia comprising the steps of:
   (a) collecting blood from a pregnant female mammal; and
   (b) detecting in said blood significantly elevated levels of at least one substance selected from the group consisting of:
      (1) a hemoglobin variant or hemoglobin variant precursor and
      (2) a red blood cell glycolytic enzyme or a red blood cell glycolytic enzyme precursor.

2. The method of claim 1 wherein said substance is selected from the group of glycated hemoglobin, hemoglobin $A_{1c}$, the $A_{1c}$–$A_O$ sum of chromatographic peak areas, phosphoglycerate kinase, low substrate % pyruvate kinase, glyceraldehyde phosphate dehydrogenase and glucose-6-phosphate dehydrogenase.

3. The method of claim 1 wherein said substance is selected from the group consisting of the $A_{1c}$–$A_O$ sum of chromatographic peak areas, glycated hemoglobin and low substrate % pyruvate kinase, and is accompanied by elevated hematocrit levels.

4. The method of claim 1 wherein said substance is a red blood cell glycolytic enzyme selected from the group consisting of phosphoglycerate kinase and low substrate % pyruvate kinase.

5. The method of claim 1 wherein said substance is low substrate % pyruvate kinase.

6. The method of claim 5 wherein the low substrate % pyruvate kinase is present at a concentration greater than about 12 IU/g Hb.

7. An assay kit for the diagnosis of preeclampsia comprising a means for detecting in the blood of a pregnant female mammal significantly elevated levels of at least one substance selected from the group consisting of:
(a) a hemoglobin variant or hemoglobin variant precursor and
(b) a blood cell glycolytic enzyme or a red blood cell glycolytic enzyme precursor.

8. The assay kit of claim 7 wherein said substance is selected from the group consisting of glycated hemoglobin, hemoglobin $A_{1c}$, the $A_{1c}$–$A_O$ sum of chromatographic peak areas, phosphoglycerate kinase, low substrate % pyruvate kinase, and is accompanied by elevated hematocrit levels.

9. The assay kit of claim 7 wherein said substances is selected from the group consisting of the $A_{1c}$–$A_O$ sum of chromatographic peak areas, glycated hemoglobin and low substrate % pyruvate kinase.

10. The assay kit of claim 7 wherein said substance is a red blood cell glycolytic enzyme selected from the group consisting of phosphoglycerate kinase and low substrate % pyruvate kinase.

11. The assay kit of claim 7 wherein said substance is low substrate % pyruvate kinase.

12. The assay kit of claim 11 wherein the low substrate % pyruvate kinase is present at a concentration greater than about 12 IU/g Hb.

13. An assay kit for diagnosing preeclampsia comprising reagents for assaying significantly elevated levels of at least one substance selected from the group consisting of:
a. a hemoglobin variant or hemoglobin variant precursor and
b. a red blood cell glycolytic enzyme or a red blood cell glycolytic enzyme precursor.

* * * * *